United States Patent [19]

Perler

[11] Patent Number: 4,986,812
[45] Date of Patent: Jan. 22, 1991

[54] LOCKING DEVICE PREVENTING REUSE OF A DISPOSABLE SYRINGE

[76] Inventor: Robert F. Perler, 25 Lockwood Ave., New Rochelle, N.Y. 10801

[21] Appl. No.: 334,710

[22] Filed: Apr. 6, 1989

[51] Int. Cl.[5] .............................................. A61M 5/00
[52] U.S. Cl. ..................................... 604/110; 604/218; 604/220
[58] Field of Search .................... 604/110, 218, 220

[56] References Cited

U.S. PATENT DOCUMENTS

| 4,212,309 | 7/1980 | Moorehead | 604/220 X |
| 4,267,846 | 5/1981 | Kontos | 604/220 X |
| 4,731,068 | 3/1988 | Hesse | 604/218 X |

Primary Examiner—John D. Yasko
Attorney, Agent, or Firm—Handal & Morofsky

[57] ABSTRACT

A non-reusable disposable syringe utilizing a conventional syringe body, a locking device allowing one full retraction of the plunger and one full expulsion of the contents wherein the locking device cooperates with the plunger shaft in advancing the piston in the expulsion stroke.

21 Claims, 3 Drawing Sheets

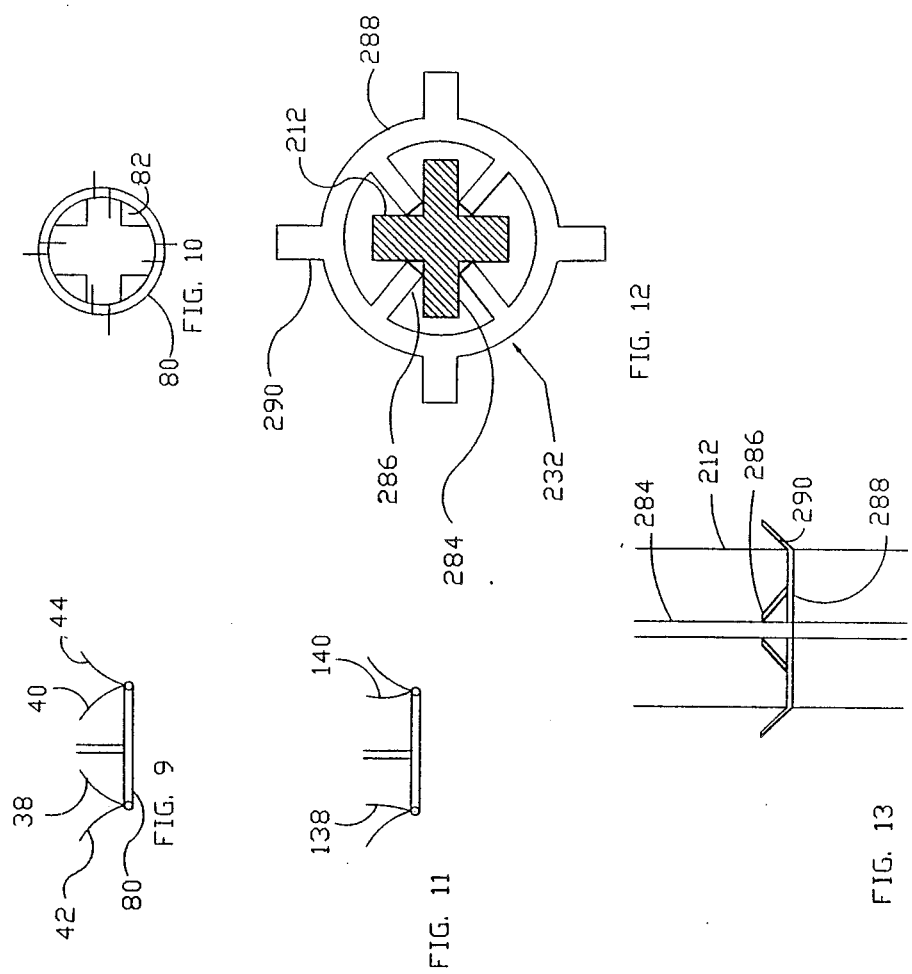

LOCKING DEVICE PREVENTING REUSE OF A DISPOSABLE SYRINGE

TECHNICAL FIELD

The present invention relates to hypodermic syringes. In particular, the invention is drawn to a disposable syringe that cannot be reused.

BACKGROUND

The increasing awareness of the importance of sterility in hypodermic devices, coupled with the continually increasing number of hypodermic injections given, has led to the advent of disposable syringes. The initial sterility and low cost of the disposable syringes has led to the widespread use of these syringes and the preference of the disposable syringes over the older reusable glass syringes that require sterilization before each use. The disposable syringe, by its very nature, has spawned problems. The disposable syringe is cheap and disposable, and controls on the inventory of a cheap and plentiful item tend to loosen while controls on discarded items have generally been lax. It is not uncommon for syringes, along with the attached needles, to find their way into unauthorized hands. The syringes may be reused without sterilization and thereby contribute to a problem they originally were designed to prevent, i.e. the spread of disease due to contamination.

An unfortunately common unauthorized use of syringes is associated with the use of illegal drugs. The common practice of sharing the syringe among drug users dramatically increases the risk of exposure to, and spread of, disease.

Hepatitis has long been associated with illegal drug use as it is spread among users of injectable drugs via contaminated hypodermic devices. Today it is known that the Human Immune Virus associated with AIDS is spread similarly. Indeed the highest rate of infection of AIDS is now found in intravenous drug users and the infection rate is increasing.

Non-reusable syringes will not stop drug use but can prevent sharing of contaminated needles and thus help fight the spread of diseases such as AIDS.

Non-reusable syringes have been designed in the past, however there are numerous shortcomings in these earlier versions. Non-retractable drive shaft or piston arrangements such as found in Butterfield, U.S. Pat. No. 4,493,703, require pre-filled syringes as the syringe may not be filled by the user in the conventional manner. Lip-and-catch mechanisms of many sorts have been proposed, however until the lip-and-catch engages, the drive shaft and piston may retract and reuse is possible. Hesse, U.S. Pat. No. 4,731,068 requires a catch to be fixedly mounted and engage a slidable sheath thus requiring additional parts within the syringe, other embodiments require a plurality of cooperating parts that add to the complexity, assembly and cost of the syringe.

Owing to the problems or costs of the previous non-reusable syringes there has been no widespread acceptance and use of these devices in the medical community.

SUMMARY OF THE INVENTION

The invention is intended to provide a remedy, retaining the advantages of sterility and low cost of the disposable syringe and incorporating a locking device preventing reuse. The device cooperates with the plunger, the piston and the syringe allowing filling, discharging and aspiration while preventing reuse and some forms of partial use or misuse.

BRIEF DESCRIPTION OF THE DRAWINGS

One way of carrying out the invention is described in detail below with reference to drawings which illustrate only two specific embodiments of the invention and in which:

FIG. 9 is a cross-section of a locking device compatible with the syringe of FIGS. 1 through 6;

FIG. 10 is a top view of a locking device;

FIG. 11 is a cross-section of a locking device compatible with the syringe of FIGS. 7 and 8;

FIG. 12 illustrates a locking device in plan; and

FIG. 13 is a view along lines 13—13 of FIG. 12.

BEST MODE FOR CARRYING OUT THE INVENTION

Figure 1:
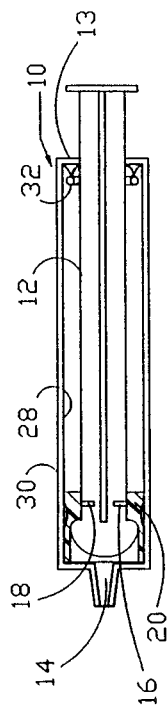
FIG. 1 is a cross section of the inventive syringe in the initial empty condition.

Referring to FIG. 1, the structure of the inventive syringe 10 is seen to comprise a plastic plunger shaft 12 integral with the plunger head 14, which is larger in diameter than the shaft, the shaft defining slots 16 and 18 to cause a weak area in the shaft forming a frangible portion. Shaft 12 is formed with a cross-section of a cross comprising four fins 19. A rubber piston 20 bears sealingly against the inner syringe wall 28 of a conventional syringe body 30. The plunger head fits within and sealingly conforms to a piston recess 22, best illustrated in FIG. 3, the rear lip 24 of plunger head 14 bearing against the recess seat 26. A shaft stabilizer 13 is secured at the end of syringe body 30.

Figure 2:
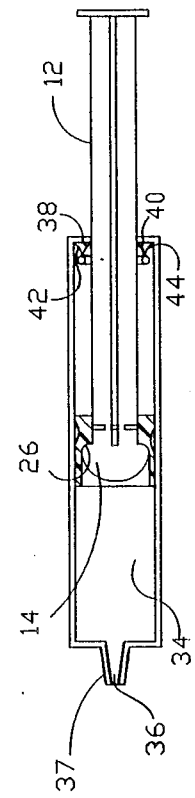
FIG. 2 is a cross-section of the syringe in FIG. 1 during the filling movement.

A spring locking device 32 is positioned at the rear of the syringe body in the initial empty condition as illustrated in FIG. 1. In this position the plunger head 14 is in the forward portion of the syringe body 30. When it is desired to use the inventive syringe; shaft 12 is pulled backwards, to draw the medicinal fluid into the syringe. FIG. 2 illustrates the plunger moving backwards. Plunger head 14 is pulled tight against recess seat 26 forming a seal and therefore reducing the pressure in the syringe interior 34 during backwards motion, drawing a fluid into the syringe interior through the needle orifice 36 within needle support 37. Plunger shaft 12 moves backwards easily over back-facing shaft prongs 38 and 40 of the locking device, while back-facing syringe prongs 42 and 44 prevent backward motion of the locking device with respect to the syringe by digging into the inner syringe wall. These prongs may terminates in a point to enhance their bite into the inner wall.

Figure 3:
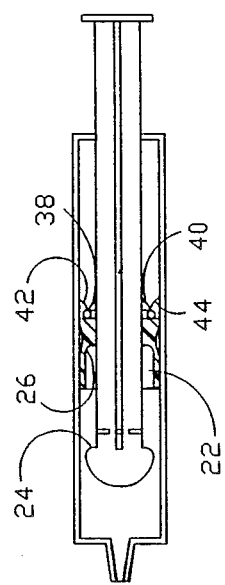
FIG. 3 is a cross-section of the syringe in FIG. 1 showing the result of an attempted premature discharge.

Forward motion of the plunger before complete retraction causes the plunger head to leave its position against recess seat 26 breaking the seal and leaving piston 20 in its position as illustrated in FIG. 3, causing leakage of the contents.

Figure 4:
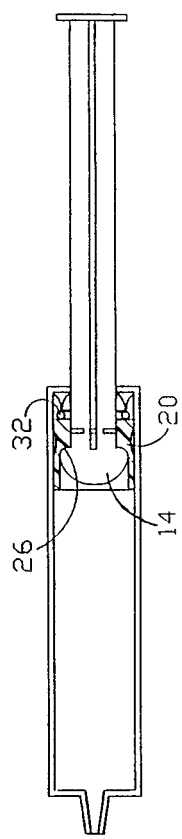
FIG. 4 is a cross-section of the syringe in FIG. 1 showing the plunger fully retracted.

The forward motion of the shaft causes it to engage shaft prongs 38 and 40, these prongs may also have pointed ends and moves the locking device forward with the shaft as syringe prongs 42 and 44 allow forward motion of the locking device with respect to the syringe. Since the prior rearward motion of shaft 12 has brought the locking device into contact with the piston, as illustrated in FIG. 4, during forward motion the forward surface of the locking device moves the piston forward with the shaft. FIG. 3 shows the positions of the locking device and the piston based upon forward motion of the shaft from the respective positions illustrated in FIG. 2.

FIG. 4 depicts the inventive syringe with shaft 12 fully retracted. Plunger head 14 is sealingly engaged against recess seat 26, and piston 20 is in forced contact with locking device 32.

Figure 5:
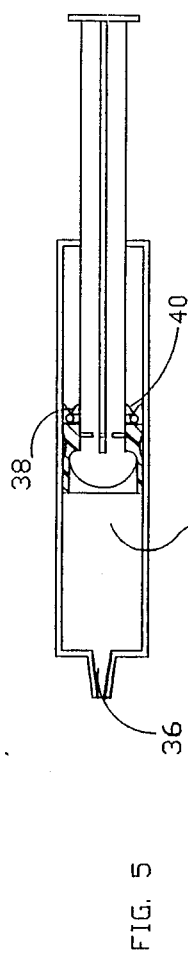
FIG. 5 is a cross-section of the syringe in FIG. 1 during the discharge motion.
Figure 6:
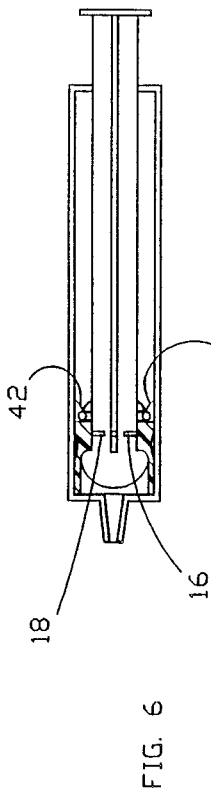
FIG. 6 is a cross-section of the syringe in FIG. 1 after complete discharge.

As the plunger shaft is moved forward prongs 38 and 40 hold the locking device in forced contact with piston 20 and plunger head 14 remains sealingly engaged against recess seat 26. The plunger shaft and head, the locking device and the piston move as a unit pressuring the contents of syringe interior 34 to move through needle orifice 36. As illustrated in FIG. 5, the locking device is moved forward by the shaft as shaft prongs 38 and 40 will not allow forward motion of the shaft with respect to the locking device. It is locking device 32 that drives piston 20 forward as the shaft is moved forward. FIG. 6 shows the syringe completely discharged. Syringe prong 42 and 44 prevent backward motion of the locking device and therefor also prevent the backward motion of the shaft and the piston. No further function is possible. Slots 16 and 18, forming the break-away construction, permit the shaft to break before the locking device moves in the situation where excess force is used in an attempt to retract the piston a second time.

Figure 7:
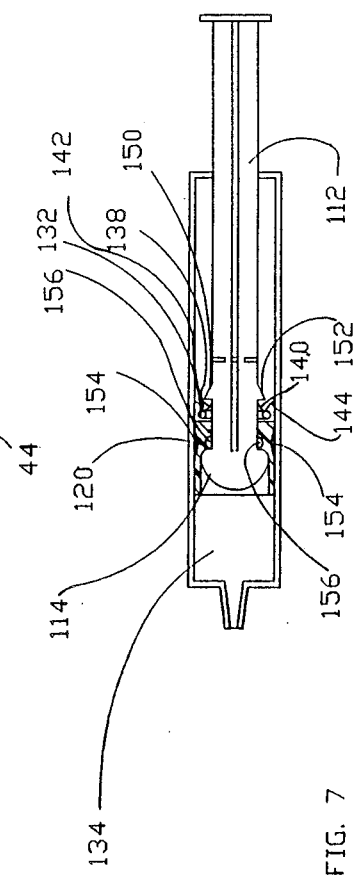
FIG. 7 is a cross-section of a second embodiment of the inventive syringe during the discharge motion.

An alternative embodiment incorporate a piston which allows aspiration with only minor changes to the design. In this embodiment, as illustrated in FIG. 7, shaft prongs 138 and 140 are modified so that no biting or digging engagement may take place with respect to plunger shaft 112. Engagement of prongs 138 and 140 with plunger shaft 112 occurs by means of catches 150 and 152 positioned on shaft 112 such that when prongs 138 and 140 engage catches 150 and 152, respectively, the locking device 132 is abutting piston 120 in the same manner as locking device 32 abuts piston 20 in FIGS. 4, 5 and 6, allowing the discharge of the fluid in the syringe interior 134.

Figure 8:
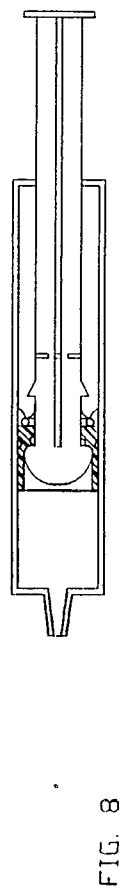
FIG. 8 is a cross-section of the syringe in FIG. 7 during aspiration.

In this embodiment piston 120 is longer than the piston of the first embodiment and has an external annular indent 154 and an internal annular hollow 156. The piston material between annular indent 154 and annular hollow 156 is sufficiently solid to hold the plunger head sealingly engaged to the piston when the assembly is advancing, the piston being pushed along by the locking device engaged on catches 150 and 152. The annular indent and the annular hollow do, however, sufficiently weaken the piston at this point to allow a flexing if the plunger head provides a backward force on the piston, as illustrated in FIG. 8. The backward force is applied by retracting the plunge shaft. Backward motion of the shaft, to the extent allowed by the piston flexing between indent 154 and hollow 156, is allowed by prongs 138 and 140 while prongs 142 and 144 hold the locking device stationary with respect to the syringe.

Release of backward force on shaft 112 allows the piston to return to the unflexed position as prongs 138 and 140 allow the shaft to move forward with respect to the locking device until catches 150 and 152 are reencountered. In this manner, aspiration may be achieved without affecting the single-use quality of the syringe or the basic mechanism employed to achieve the single-use aspect of the inventive syringe. Aspiration is a means of determining whether or not the needle is in a blood vessel.

The locking device may consist of a ring 80 or other shape allowing the plunger shaft to pass through its center with resilient wire prongs attached to the ring, as illustrated in FIGS. 9 and 10. Alignment members 82 may also be incorporated. Flattened or planar members may be used instead of wire. The ring may be constructed of metal or plastic, the prongs are preferably formed from metal. The wire used may be spring steel and may be welded or soldered to a metal ring or may be stamped integrally therewith. The prongs may be pointed to enhance their "biting" ability. However, in the case of the embodiment shown in FIGS. 7 and 8, sharpening of the inner-directing, shaft prongs such as 138 and 140 is to be avoided (FIG. 4). Additionally, the prongs are to be shaped to avoid digging into the cylindrical shaft but capable of engaging the catches positioned on the shaft. A self-aligning stamped star-washer type of locking member 232 is illustrated in FIG. 12. Here the shaft 212, shaped as a cross in cross-section has inner rounded surfaces 284 which engage inner gripping members 286 mounted on ring 288 which is integral with outer gripping member 290. As can be seen from FIG. 18, locking member 232 can be stamped from reliant sheet metal. The slots forming the frangible portion of the shaft may be placed behind the point where the locking device prongs engage the shaft so that the break-away construction may serve to prevent forced twisting of the shaft to loosen the bite that the locking device ma have on the cylinder or shaft, as illustrated in phantom lines in FIG. 7 and 8. In this manner the shaft will separate into two parts before the twisting motion is significantly transferred to the locking device which may adversely affect the device's function.

The syringe and the plunger shaft are constructed of the normal materials associated with disposable syringes now in use, i.e. plastics or polymers and copolymers such as polyethylene, polypropylene, polystyrene, polybutylstyrene, etc.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A locking device for use in a plastic disposable syringe body with an open end, and fitting around a plunger shaft associated with said syringe body, comprising:

(a) a base, proportioned to fit within said syringe body, said base defining a central opening sufficiently large such that said plunger shaft may pass through said opening;

(b) a syringe prong integrally associated with said base, extending from said base in an axial direction and radially outwardly to an extent that said syringe prong contacts said syringe body when said locking device is positioned in said syringe body; and (c) a shaft prong integrally associated with said base, extending from said base in the same axial direction as said syringe prong and extending radially inwardly to an extent that said shaft prong contacts said plunger shaft when said plunger shaft is within said central opening.

2. A locking device as claimed in claim 1, wherein said locking device further comprises three additional syringe prongs and three additional shaft prongs arranged at 90° intervals around said base, said base being substantially circular in configuration.

3. A locking device as claimed in claim 1, wherein said syringe prongs have pointed tips.

4. A locking device as claimed in claim 2, wherein said base in annular and said syringe prongs and said shaft prongs are comprised of metal.

5. A locking device as claimed in claim 4, wherein said syringe prongs, said shaft prongs and said base are formed from a single piece of sheet metal, said shaft prongs being positioned, configured and dimensioned to engage the juncture between fins of a multifinned shaft.

6. A looking device as claimed in claim 4, wherein said syringe prongs and said shaft prongs are welded to said base.

7. A non-reusable disposable syringe comprising:
(a) a syringe body having an open end and defining an inside surface;
(b) a plunger comprising a plunger shaft and a plunger head;
(c) a cylindrical piston dimensioned and configured such that said piston bears sealingly against the inside surface of said syringe body said piston being positioned within said syringe body, aid piston defining a central passage, a portion of said central passage being smaller than said plunger head, and said central passage being configured and dimensioned to sealingly engage and be closed by said plunger head, said piston being positioned within said syringe body with said plunger passing into said central passage; and
(d) a locking device supported for slidable movement with respect to said plunger, said locking device being capable of movement with respect to said plunger in one direction only and capable of movement with respect to said syringe body in only one direction, said locking device being configured and dimensioned to advance said piston with said plunger after said piston is brought into contact with said locking device.

8. A non-reusable disposable syringe as in claim 7, wherein said locking device comprises:
(a) a base, proportioned to fit within said syringe body, said base defining a central opening sufficiently large such that said plunger shaft may pass through said opening;
(b) a plurality of syringe prongs integrally associated with said base, extending from said base in an axial direction and radially outwardly to an extent that at least one of said syringe prongs contact said syringe body when said locking device is positioned in said syringe body; and (c) a plurality of shaft prongs integrally associated with said annular base, extending from said base in the same axial direction as said syringe prongs and also extending radially inwardly to an extent that at least one of said shaft prongs will contact said plunger shaft when said plunger shaft is within said central opening.

9. A non-reusable disposable syringe as in claim 7, wherein said plunger shaft defines a break-away construction.

10. A non-reusable disposable syringe as in claim 8, wherein said axial direction extends toward the open end of said syringe body.

11. A non-reusable disposable syringe as in claim 10, wherein said plunger head initially substantially abuts a closed end of said syringe body opposite said open end, and wherein said locking device is positioned adjacent said open end.

12. A non-reusable disposable syringe as in claim 9, wherein said break-away construction comprises slots cut into said plunger shaft.

13. A non-reusable disposable syringe as in claim 12, wherein sad slots are placed upon said shaft such that sad locking device may be positioned between said piston and said slots.

14. A non-reusable disposable syringe as in claim 7, wherein said shaft comprises catches to engage said shaft prongs and hold said locking device in forced contact with said piston.

15. A non-reusable disposable syringe as in claim 7, wherein said syringe further comprises a plunger shaft stabilizer.

16. A non-reusable disposable syringe comprising:
(a) a plastic syringe body comprising an open end, a substantially closed end forming a needle support and defining a needle orifice, and an interior surface defining an interior volume;
(b) a plunger comprising a plunger shaft, a plunger head, said plunger head being of greater diameter than said plunger shaft, raised catches on said plunger shaft near said plunger head, and a frangible portion;
(c) a plunger shaft stabilizer positioned at said open end of said syringe body;
(d) an cylindrical piston dimensioned and configured such that said piston bears sealingly against said syringe body when inserted within said syringe body, said piston comprising a central passage sufficiently large to accommodate said plunger shaft and, at a point insufficient to accommodate said plunger head and capable of sealingly engaging said plunger head and positioned with said plunger shaft passing through said central passage; and
(e) a locking device comprising:
(i) a base, proportioned to fit within said syringe body, said base defining a central opening sufficiently large such that said plunger shaft may pass through said opening;
(ii) a plurality of syringe prongs integrally associated with said base, extending from said base in an axial direction and radially outwardly to an extent that at least one of said syringe prongs contact said syringe body when said locking device is positioned in said syringe body and allow movement of said base in one direction only with respect to said syringe body, said direction being towards said substantially closed end; and (iii) a plurality of shaft prongs integrally associated with said annular base, extending from said base in the same axial direction as said syringe prongs and also extending radially inwardly to the extent that at least one of said shaft prongs will contact said plunger shaft when said plunger shaft is within said central opening and will lockingly engage with said raised catches holding said locking device in forced contact with said piston.

17. A non-reusable disposable syringe as claimed in claim 16, wherein said locking device comprises four syringe prongs and four shaft prongs.

18. A non-reusable disposable syringe as claimed in claim 16, wherein said syringe prongs have sharp pointed tips.

19. A locking device as claimed in claim 16, wherein said annular base and said syringe prongs and said shaft prongs are comprised of metal.

20. A non-reusable disposable syringe as claimed in claim 14, wherein said piston has an annular external indent and a concentric interior annular hollow resulting in a thin area of said piston between said indent and said hollow such that said thin area is capable of flexing when said piston is forced back against said locking device, capable of returning to an at rest condition when the back force is removed and capable of retaining the at rest condition when said piston is forced by only said locking device.

21. A non-reusable disposable syringe as claimed in claim 16, wherein said piston has an annular external indent and a concentric interior annular hollow resulting in a thin area of said piston between said indent and said hollow such that said thin area is capable of flexing when said piston is forced back against said locking device, capable of returning to an at rest condition when the back force is removed and capable of retaining the at rest condition when said piston is forced by only said locking device.

* * * * *